United States Patent

Jansen et al.

[11] Patent Number: 5,144,009
[45] Date of Patent: * Sep. 1, 1992

[54] CONJUGATES IN WHICH A MONOVALENT CARBOXYLIC IONOPHORE IS ASSOCIATED BY MEANS OF A COVALENT BOND WITH A MACROMOLECULE, THEIR USE AS IMMUNOTOXIN POTENTIATORS AND THE INTERMEDIATE ACTIVATED INOPHORES

[75] Inventors: Franz Jansen, Castries; Pierre Gros, Montpellier, both of France

[73] Assignee: Sanofi, Paris, France

[ * ] Notice: The portion of the term of this patent subsequent to Sep. 17, 2007 has been disclaimed.

[21] Appl. No.: 458,444

[22] Filed: Dec. 28, 1989

Related U.S. Application Data

[60] Division of Ser. No. 34,712, Apr. 6, 1987, Pat. No. 4,919,928, which is a continuation of Ser. No. 733,660, May 13, 1985, abandoned.

[30] Foreign Application Priority Data

May 23, 1984 [FR] France ................. 84 08073
Jul. 13, 1984 [FR] France ................. 84 11208

[51] Int. Cl.$^5$ .............. C07K 17/02; C07K 15/14; A61K 39/44

[52] U.S. Cl. ................. 530/363; 530/300; 530/345; 530/370; 530/391.1; 530/391.9; 530/402; 530/403; 530/404; 530/405; 530/406; 530/399; 530/408; 530/409; 530/410; 424/85.91; 424/85.8; 514/8; 514/12

[58] Field of Search .......... 530/390, 391, 404, 405, 530/363, 388, 384, 406, 345, 402, 403, 408, 409, 410, 370, 300, 399.3, 391.9, 391.1; 514/885, 12, 8; 424/85.91, 85.8

[56] References Cited

U.S. PATENT DOCUMENTS

4,767,621  8/1988  Jansen et al. .......... 424/85.91
4,919,928  4/1990  Jansen et al. .......... 424/85.91

OTHER PUBLICATIONS

The Merck Index, product No. 6081, p. 810 Ninth edition, 1976 Merck & Co., Inc. Rahway, NJ.

*Primary Examiner*—Christine M. Nucker
*Assistant Examiner*—Kay K. Kim
*Attorney, Agent, or Firm*—Bacon & Thomas

[57] ABSTRACT

The present invention relates to conjugates in which a monovalent carboxylic ionophore is associated by means of a covalent bond with a macromolecule chosen from antibodies, fragments of antibodies, proteins such as peptide hormones or human proteins, and peptide ligands. It also relates to the activated inophores.

These conjugates are suitable as immunotoxin potentiators.

17 Claims, No Drawings

CONJUGATES IN WHICH A MONOVALENT CARBOXYLIC IONOPHORE IS ASSOCIATED BY MEANS OF A COVALENT BOND WITH A MACROMOLECULE, THEIR USE AS IMMUNOTOXIN POTENTIATORS AND THE INTERMEDIATE ACTIVATED INOPHORES

This application is a division of application Ser. No. 07/034,712, filed Apr. 6, 1986 now U.S. Pat. No. 4,919,928 which is a continuation of Ser. No. 06/733,660, filed May 13, 1985 (now abandoned).

The present invention relates to new conjugates in which a monovalent carboxylic ionophore is associated by means of a covalent bond with a macromolecule. It also relates to the application of the said conjugates as immunotoxin potentiators.

The present invention further relates to the activated ionophores as intermediates in the synthesis of the said conjugates.

In its earlier patent application filed in France under No. 82/02 091, the Applicants mentioned the capacity of carboxylic ionophores to potentiate immunotoxins.

The term "immunotoxins" denotes anticancer substances obtained by the coupling, by means of a covalent bond, of a cytotoxic protein (for example the A chain of ricin) with antibodies or fragments of antibodies directed against an antigen carried by a cell to be destroyed.

Such immunotoxins have been described especially by the Applicants in French Patent No. 78/27838 and its Addition No. 79/24655 and in French Applications No. 81/07596 and No. 81/21836. It has been possible advantageously to use the potentiating properties of ionophores in certain types of situations. In particular, they give favorable results whenever an immunotoxin is used as a selective cytotoxic agent in vitro for destroying the target cells, especially when the immunotoxin is used as a cytotoxic agent in the treatment of the bone marrow of leukemia patients into whom the bone marrow treated in this way is subsequently to be transplanted. It is also the case when the immunotoxin is used to reduce the population of T cells in a graft for bone marrow allograft applications for the purpose of preventing the disorders associated with the reaction of the graft against the host.

By contrast, when the immunotoxin is used in vivo as a therapeutic agent in man, the in vivo use of an ionophore to profit from the potentiating effect is subject to certain limitations which are inherent in:

the toxicity peculiar to the ionophores;
their low solubility in the solvents appropriate for parenteral administrations; and
their very rapid elimination from the blood plasma.

According to the present invention, it has been found that, surprisingly, these limitations can be overcome by replacing the carboxylic ionophores with conjugates in which a monovalent carboxylic ionophore is associated by means of a covalent bond with a macromolecule such as an antibody, a fragment of an antibody, a protein, a peptide or alternatively a mixed macromolecule obtained by the covalent coupling of an antibody with a protein.

According to a first feature, the present invention therefore relates, by way of new products, to conjugates (mixed artificial molecules) formed by the covalent bonding of a monovalent carboxylic ionophore with macromolecules (such as antibodies, proteins or peptide ligands).

In the remainder of the present description, such conjugates will be referred to as "ionophoric conjugates".

The ionophores used are known molecules, especially natural substances isolated from strains of Streptomycetes fungi which contain a hydrocarbon skeleton incorporating oxygen heterocycles. There is always a carboxylic acid group at one end of the chain and there are one or more alcohol groups at the other end (B. C. Pressman, Annual review of Biochemistry, 45, 501–530, 1976).

These natural substances, as well as certain semisynthetic compounds derived therefrom, share an ionophoric activity, i.e. the capacity to enable metal ions (especially monovalent ions) to be transferred from a hydrophilic phase to a lipophilic phase, the said phases being immiscible.

The macromolecules used can be antibodies (or fragments of antibodies), proteins (such as peptide hormones or human proteins, for example human serum albumin), peptide ligands (such as natural or synthetic polypeptides and in particular polylysine) or alternatively mixed macromolecules obtained by the covalent coupling of an antibody with a protein.

In the case where an antibody is used, this can be either of a polyclonal nature, if it results from conventional immunization carried out on an animal, or of a monoclonal nature, if it is produced by a clone of hybrid cells obtained by fusion between lymphocytes and myeloma cells. This antibody can be used either in the form of whole immunoglobulin molecules having the capacity to recognize the chosen antigen, or in the form of any fragment of these immunoglobulin molecules which has retained the capacity to recognize the chosen antigen, in particular the fragments known as F(ab')$_2$, Fab and Fab'.

The chemical coupling of the macromolecules with the ionophore can be carried out by a variety of methods with the proviso that the chosen method:

preserves the respective biological activities of the components of the conjugate;
ensures a satisfactory reproducibility and a good coupling yield;
makes it possible to control the value of the ratio ionophore/macromolecule in the conjugate obtained; and
leads to a stable and water-soluble product.

Among all the chemical coupling methods corresponding to these characteristics, it is possible to choose those which involve one or more thiol groups for forming the bond. In this case, it is possible to use a thiol group which has been introduced artificially into one of the compounds to be coupled, and to introduce into the other compound one or more groups which are capable of reacting with the thiol groups, in an aqueous medium with a pH of between 5 and 9, at a temperature not exceeding 30° C., to produce a stable, covalent and clearly defined bond.

For example, a thiol can be introduced artificially into the ionophores by reaction with S-acetylmercaptosuccinic anhydride, which will be capable of acylating one of the alcohol groups of the ionophore. It will then be possible to free this thiol group by reaction with hydroxylamine to remove the acetyl protecting radical, in the manner already described (Archives of Biochemistry and Biophysics, 119, 41–49, 1967).

Suitable ionophores are monensin, nigericin, grisonixin and lasalocid; particular preference is given to monensin and nigericin, which have the formulae:

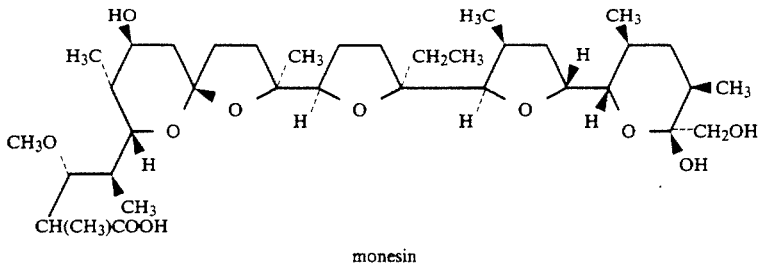

monesin

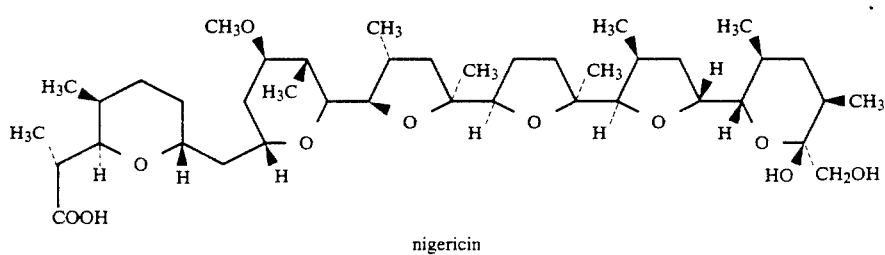

nigericin

The artificial introduction of the thiol is carried out by reacting the ionophore with S-acetylmercaptosuccinic anhydride of the formula:

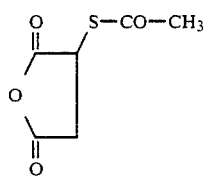

in an inert organic solvent at approximately ambient temperature.

This reaction forms an ester bond between one of the hydroxyls of the ionophore, which is the primary hydroxyl in the case of monensin and nigericin, and the acetylmercaptosuccinic acid to give a compound of the formula:

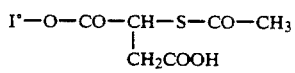   I in which I° represents the residue of the ionophore from which one of the hydroxyls, which is the primary hydroxyl in the case of monensin and nigericin, has been removed.

The thiol group of the above compound can be freed by reaction with hydroxylamine, and the resulting product of the formula:

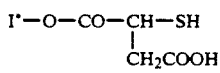   II in which I° is as defined above, can be used in situ for the coupling operation.

The said activated ionophores, which are represented by the formula:

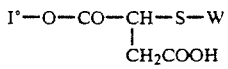   III

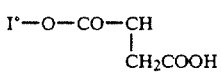

in which W is hydrogen or an acetyl group, are new and represent another feature of the present invention.

The group:

$$I^\circ-O-CO-CH \\ \quad\quad\quad\quad | \\ \quad\quad\quad\quad CH_2COOH$$

is indicated hereafter as I and denotes "the ionophore to be coupled".

The coupling with the macromolecule can be carried out with one or other of the compounds I and II, but the said coupling is faster with compound II, the use of which is therefore preferred.

The coupling will thus be carried out with the macromolecule into which one or more groups capable of forming a covalent bond with the thiol have been introduced. This covalent bond may be either a disulfide bond or a thioether bond.

The Disulfide Bond

In this case, the preparation of the conjugate can be represented by the equation:

in which:
 I represents the ionophore to be coupled,
 P represents the macromolecule to be modified and
 —S—S—X denotes an activated mixed disulfide group, X being the activating radical.

The macromolecule substituted by an activated sulfur atom is obtained from the macromolecule itself by substitution with the aid of a reagent which itself carries an activated sulfur atom, according to the equation:

in which:
 P is the macromolecule to be modified,

Y represents a group permitting the covalent fixation of the reagent to the protein, R denotes a group capable of carrying the substituents Y and —S—S—X simultaneously, and X denotes the activating radical.

The functional group Y is a group capable of bonding covalently with any one of the groups carried by the side chains of the constituent amino acids of the protein to be substituted. Among these groups, the terminal amino groups of the lysyl radicals contained in the protein are particularly recommended. In this case, Y can represent especially:

- a carboxyl group which can bond to the amino groups of the protein in the presence of a coupling agent such as a carbodiimide and especially a water-soluble derivative like 1-ethyl-3-diethylaminopropyl-3-carbodiimide,
- a carboxylic acid chloride which is capable of reacting directly with the amino groups to acylate them,
- a so-called "activated" ester such as an ortho- or para-nitrophenyl or -dinitrophenyl ester, or alternatively an N-hydroxysuccinimide ester, which reacts directly with the amino groups to acylate them,
- an internal anhydride of a dicarboxylic acid, such as, for example, succinic anhydride, which reacts spontaneously with the amine groups to create amide bonds, or
- an imidoester group:

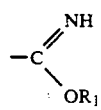

in which $R_1$ is an alkyl group reacting with the amino groups of the macromolecule according to the equation:

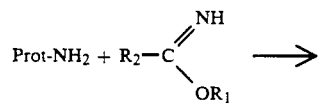

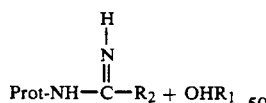

The radical —S—S—X denotes an activated mixed disulfide capable of reacting with a free thiol radical. In particular, in the mixed disulfide, X can denote a pyridin-2-yl or pyridin-4-yl group optionally substituted by one or more alkyl, halogen or carboxyl radicals. X can also denote a phenyl group preferably substituted by one or more nitro or carboxyl groups. Alternatively, X can represent an alkoxycarbonyl group such as the methoxycarbonyl group.

The radical R denotes any radical capable of carrying the substituents Y and —S—S—X simultaneously. It must be chosen so as not to contain groups capable of interfering, during the subsequent reactions, with the reactants used and the products synthesized. In particular, the group R can be a group —(CH$_2$)$_n$, n being between 1 and 10, or alternatively a group:

in which $R_4$ denotes hydrogen or an alkyl group having from 1 to 8 carbon atoms and $R_3$ denotes a substituent which is inert towards the reactants to be used subsequently, such as a carbamate group:

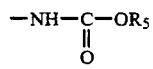

in which $R_5$ denotes a linear or branched alkyl group having from 1 to 5 carbon atoms, especially the tert.-butyl group.

The reaction of the compound Y—R—S—S—X with the macromolecule P is carried out in a homogeneous liquid phase, most commonly in water or a buffer solution. If necessitated by the solubility of the reactants, up to 30% by volume of a water-miscible organic solvent, such as an alcohol and especially tertiary butanol, can be added to the reaction medium. The reaction is carried out at ambient temperature for a time varying from a few minutes to 24 hours, after which the low molecular weight products, and in particular the excess reactants, can be removed by dialysis. This process usually makes it possible to introduce between 1 and 50 substituents per mol of macromolecule.

When using such compounds, the coupling of the macromolecule with the ionophore is carried out by bringing the two compounds together in aqueous solution, at a temperature not exceeding 30° C., for a time varying from a few minutes to 1 day. The aqueous solution obtained is dialyzed to remove the low molecular weight products.

THE THIOETHER BOND

In this case, the preparation of the conjugate consists in reacting I—SH with the protein P into which a maleimide radical has been introduced beforehand. The reaction is then represented by the equation:

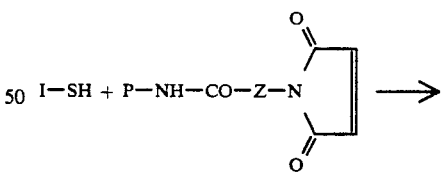

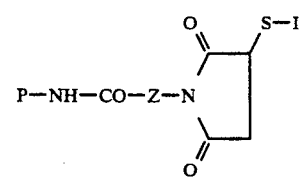

in which: Z represents an aliphatic or aromatic spacing structure containing from 1 to 10 carbon atoms.

The protein P substituted by maleimide is obtained from the protein P itself by substitution of amino groups of the protein with the aid of a reagent which itself carries the maleimide group, according to the equation:

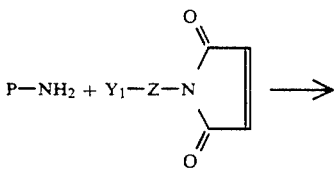

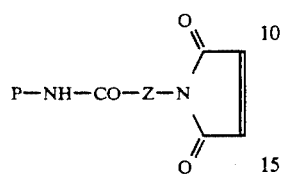

in which $Y_1$ represents:
either a carboxyl group, in which case the reaction is carried out, after activation of the carboxyl group, in the presence of a coupling agent such as a carbodiimide and especially a water-soluble derivative such as 1-ethyl-3-diethylaminopropyl-3-carbodiimide,
or a so-called "activated" ester such as an ortho- or para-nitrophenyl or -dinitrophenyl ester, or alternatively an N-hydroxysuccinimide ester, which reacts directly with the amino groups to acylate them.

The preparation of such reagents is described especially in Helvetica Chimica Acta, 58, 531-541 (1975). Other reagents in the same class are commercially available.

The reaction of the compound:

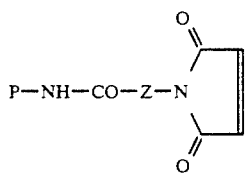

with the ionophore is carried out in a homogeneous liquid phase, most commonly in water or a buffer solution. If necessitated by the solubility of the reactants, up to 20% by volume of a water-miscible organic solvent, such as an alcohol and especially tertiary butanol, can be added to the reaction medium.

The reaction is carried out at ambient temperature for a time varying from a few hours to 24 hours, after which the low molecular weight products, and in particular the excess reactants, can be removed by dialysis. This process usually makes it possible to introduce between 1 and 50 substituent groups per mol of protein.

When using such compounds, the coupling of the macromolecule with the ionophore is carried out by bringing the two compounds together in aqueous solution, at a temperature not exceeding 30° C., for a time varying from a few hours to one day. The solution obtained is dialyzed to remove the low molecular weight products, and the conjugate can then be purified by a variety of known methods.

According to a second feature, the invention relates to the use of the ionophoric conjugates as immunotoxin potentiators. It also relates to the medicinal associations in which at least one immunotoxin and at least one ionophore according to the invention are present.

Studies performed on the ionophoric conjugates have shown that:
the potentiating effect of the ionophores is preserved after coupling with the macromolecule.
The bonding of the ionophore to the macromolecule provides the former with a high solubility in aqueous media, which favors in vivo administration of the product.
the bonding of the ionophore to the macromolecule considerably increases the plasma half-life of the ionophore, which is essential for maintaining the potentiating effect in vivo;
the toxicity of the conjugate is lower than that of the ionophore alone.
Thus, for each patient, at least two effectors essential for achieving the result will be directed towards the target cells:
firstly a cytotoxic protein (such as, for example, the A chain of ricin), which will be the cytotoxic effector incorporated in the so-called immunotoxic conjugate; and
secondly the ionophore (such as, for example, monensin), which is the constituent of the potentiating system incorporated in the so-called "ionophoric conjugate".

In the case where the ionophore is coupled with a macromolecule possessing a receptor on the surface of the target cells (for example when the macromolecule is an antibody or a fragment of an antibody recognizing an antigen specific for the cell population to be destroyed which is different from that recognized by the immunotoxin), or alternatively if the ionophore is coupled with a peptide hormone possessing a receptor on the surface of the cells to be destroyed, the probability that both the chosen targets will be present together on the surface of the non-target cells becomes very low, thus affording an extremely powerful method for further increasing the specific nature of the cytotoxicity of immunotoxins.

The examples which follow illustrate the invention without limiting its scope.

EXAMPLE 1

Ionophoric conjugate obtained by reacting the antibody T 29-33 substituted by an activated disulfide group with monensin into which a thiol has been introduced.

A) ANTIBODY T 29-33

This antibody is a monoclonal antibody directed against the antigen T 200 of human leukocytes. This antibody is described in J. Exp. Med., 1980, 152, 842. It is commercially available from Hybritech Inc., San Diego-Calif.-U.S.A.

B) ACTIVATED ANTIBODY T 29-33

An aqueous solution containing 3 mg of 3-(pyridin-2-yldisulfanyl)propionic acid, dissolved in tertiary butanol beforehand, and 1.8 mg of 1-ethyl-3-dimethylaminopropyl-3-carbodiimide is added to 2 ml of a solution of antibody T 29-33 containing 10 mg/ml (i.e. 0.133 μmol) of antibody. The mixture is stirred for 15 minutes at 30° C. and then dialyzed continuously against 125 mM phosphate buffer of pH 7 (40 hours at 500 ml/hour). After dialysis, the protein solution is centrifuged to give 2.5 ml of a solution containing 6.6 mg of modified antibody per ml. By spectrophotometric analysis at 343 nm of the pyridine-2-thione released by exchange with 2-mercaptoethanol, it is found that the antibody obtained carries 7.2 activating groups per mol of antibody.

C) ACTIVATED MONENSIN

The monensin used is a commercial product. It was modified as follows: 693 mg of monensin are dissolved in chloroform and then reacted with 350 mg of S-acetyl-mercaptosuccinic anhydride (SAMSA). The reaction is left to proceed for ½ hour at ambient temperature. The reaction medium is subsequently evaporated to dryness in vacuo, the residue is then taken up in ethyl acetate and the mixture is washed extensively with water. The organic phase is then dried and pumped to dryness in vacuo. The product is obtained in crystalline form after drying in vacuo. It is identified by its NMR spectrum and its mass spectrum.

The product thus obtained (S-acetyl activated monensin) has the formula III above in which I° is the residue of monensin from which the primary hydroxyl has been removed, and W is an acetyl group.

The acetyl radical can be released by reaction with hydroxylamine at a final concentration of 50 mM, and the product thus obtained, corresponding to the formula III above in which I° is the residue of monensin from which the primary hydroxyl has been removed, and W is hydrogen, can be used directly for the coupling operation.

However, for the next step, it is preferable to free the thiol group in situ in the presence of the S-acetyl activated monensin and the activated antibody.

D) PREPARATION OF THE IONOPHORIC CONJUGATE 8 mg (i.e. 9 μmol) of S-acetyl activated monensin are dissolved in the minimum quantity of tert.-butanol and the solution is added to 2.5 ml of a solution of activated antibody containing 6.6 mg/ml (i.e. 0.11 μmol) in 125 mM phosphate buffer of pH 7. 125 μl of a 1N hydroxylamine solution are added.

Incubation takes 2 hours at 25° C. and the reaction medium is then purified to remove excess reactants by dialysis against PBS buffer (10 mM in respect of phosphate, 140 mM in respect of sodium chloride, pH 7.4).

Dialysis and centrifugation gave 2.8 ml of a solution of IgG T 29-33 containing 5.6 mg/ml, carrying an average of 7 monensins per mol of antibody.

EXAMPLE 2

Potentiation of the immunotoxin anti-T65.

The conjugate according to the invention, obtained as indicated above, was studied for its biological properties and more especially its capacity to potentiate the activity of the immunotoxin anti-T65 in a suitable cell model.

This model consists of cells of the CEM human lymphoblastoid line which naturally carry the antigens T65 and T200. The antigen T65, against which the immunotoxin used is directed, constitutes the first target antigen of the model. This immunotoxin is the one described in a previous patent application in the name of the Applicants, filed in France under No. 81/21836. The antigen T200, against which the ionophoric conjugate is directed, will be the second target antigen of the model.

As the fundamental property of immunotoxins is to inhibit the protein synthesis of the target cells, the test used consists in measuring the effect of the substances studied on the incorporation of $^{14}C$-leucine into the cancerous cells in culture. This measurement is carried out by a technique adapted from the one described in Journal of Biological Chemistry, 1974, 249 (11), 3557-3562, using the tracer $^{14}C$-leucine to determine the degree of protein synthesis. The radio-activity incorporated is determined here on the whole cells isolated by filtration.

On the basis of these determinations, it is possible to draw the dose/effect curves, plotting, on the abscissa, the molar concentration of A chain in the substances studied, and, on the ordinate, the incorporation of $^{14}C$-leucine expressed as a percentage of the incorporation by the control cells in the absence of any substance affecting protein synthesis.

It is thus possible to determine, for each substance studied, the concentration which inhibits the incorporation of $^{14}C$-leucine by 50%, or "50% inhibitory concentration" ($IC_{50}$).

The various experiments were carried out in the following manner; the corresponding experimental results are shown in FIG. 1.

a) CEM cells are incubated for 18 hours in the presence of known concentration of immunotoxin anti-T65 used as the reference, and the cells are then subjected to the step for incorporation of the radio-active tracer. The $IC_{50}$ obtained is $2.8 \cdot 10^{-11}M$ (curve 1), which shows that the cells have a normal sensitivity to the effect of the immunotoxin.

b) The CEM cells are incubated for 18 hours at 37° C. in the presence of a mixture of known concentrations of immunotoxin anti-T65 and respectively:

1—either free monensin at a concentration of 50 nM (curve 2),

2—or ionophoric conjugate anti-T200, already described, at a concentration of $10^{-8}M$ (i.e. 70 nM in respect of monensin) (curve 3).

A check was carried out beforehand to show that monensin and the ionophoric conjugate were not cytotoxic to the cells employed at the concentrations indicated.

The $IC_{50}$ values obtained are respectively:
$2.4 \cdot 10^{-14}M$ for 50 nM monensin
$1.4 \cdot 10^{-14}M$ for $10^{-8}M$ ionophoric conjugate.

These results show remarkable potentiating effects with a factor of 1000 times for 50 nM monensin and 2000 times for the ionophoric conjugate at a concentration of $10^{-8}M$ (i.e. 70 nM in respect of monensin).

EXAMPLE 3

Ionophoric conjugate obtained by reacting the antibody 3E10 substituted by an activated disulfide group with monensin into which a thiol has been introduced.

A) ANTIBODY 3E10

This antibody is a monoclonal antibody directed against a human membrane antigen. It was obtained from a lymphocytic fusion inhibiting SK MEL 28 human melanoma cells. The hybridoma was cloned and multiplied; the antibody was produced in ascitic fluid and then purified on Sepharose protein A.

B) ACTIVATED ANTIBODY ANTI-3E10

This antibody is obtained from the above antibody by a technique described in Example 1, giving 195 mg of antibody 3E10 possessing 8 activating groups per mol of antibody.

C) ACTIVATED MONENSIN

The monensin is activated by the method described in Example 1.

D) PREPARATION OF THE IONOPHORIC CONJUGATE 91 mg of S-acetyl activated monensin (i.e. 104 μmol) are dissolved in the minimum quantity of tert.-butanol and added to 50 ml of a solution of activated antibody containing 3.9 mg/ml (i.e. 1.3 μmol) in 125 mM phosphate buffer of pH 7. 2.5 ml of a 1N hydroxylamine solution are added.

Incubation takes 2 hours at 25° C. and the reaction medium is then purified to remove excess reactants by dialysis against PBS buffer (10 mM in respect of phosphate, 140 mM in respect of sodium chloride, pH 7.4). Dialysis and centrifugation gave 2.8 ml of a solution of IgG containing 3.7 mg/ml, carrying an average of 8 monensins per IgG.

EXAMPLE 4

Toxicity of the conjugate 3E10/monensin.

The conjugate 3E10/monensin was studied for its biological properties in vivo. More especially, its toxicity and its pharmacokinetics were compared with those of free monensin.

The toxicity of free monensin was determined on mice. The 50% lethal dose after intravenous injection is 4 mg/kg, i.e. 80 μg/mouse.

The toxicity of the conjugate was tested on mice in a single administration, also intravenously. The product was injected intravenously at the following doses to the mice in each group: 3.7 mg, 1.85 mg, 0.952 mg and 0.496 mg of conjugate, i.e. the equivalent of 163 μg, 81.5 μg, 40.75 μg and 20.4 μg of monensin respectively. No mortality was observed in any of the groups of mice.

EXAMPLE 5

Pharmacokinetics of the conjugate 3E10/monensin.

The pharmacokinetics were studied on female nude mice using the ionophoric conjugate described in Example 3.

The mice are injected with the following:
either 1 ml of ionophoric conjugate containing 3.7 mg/ml (i.e. 163 μg of coupled monensin),
or 163 μg of free monensin (control group).

At each time, the plasmas of two mice are sampled. The active monensin is determined in the plasmas by dilution of the latter and comparison with a standard curve for free monensin in the test for the inhibition of protein synthesis, described in Example 1.

The determination is performed on CEM cells in the presence of the immunotoxin anti-T65.

The results are given in FIG. 2, in which the time in hours has been plotted on the abscissa and the monensin concentration in μg/ml has been plotted on the ordinate. These results show that:

1) the free monensin cannot be detected in the plasmas (except at time zero, when a plasma concentration of $5 \cdot 10^{-7}$ M, i.e. about 0.5 μg/ml, is found, which corresponds to a quantity of 0.007% of the injected dose in the total mass of blood in the mouse); and 2) the conjugate can be detected for at least 8 hours at a concentration of the order of 10 μg/ml, i.e. about $1 \cdot 10^{-5}$ M.

After 24 hours, the concentration found is now only of the order of 1.5 μg/ml. This concentration is nevertheless 100 times greater than that necessary for maximum activation under the conditions of the in vitro experiments.

EXAMPLE 6

Ionophoric conjugate obtained by reacting human serum albumin (SA) substituted by an activated disulfide group with monensin into which a thiol has been introduced.

A) ACTIVATED HUMAN SERUM ALBUMIN

The SA was obtained from the above SA by a technique analogous to that described for the antibodies in the previous examples, giving 220 mg of SA possessing 16 activating groups per mol of albumin.

B) ACTIVATED MONENSIN

The monensin is activated by the method described in Example 1.

C) PREPARATION OF THE IONOPHORIC CONJUGATE 228 mg of S-acetyl activated monensin, i.e. 268 μmol, are dissolved in the minimum quantity of tert.-butanol and added to 23 ml of a solution of activated SA containing 9.4 mg/ml (i.e. 52.7 μmol) in 125 mM phosphate buffer of pH 7. 1.15 ml of a 1N hydroxylamine solution are added.

Incubation takes 1 hours at 25° C. and the reaction medium is then dialyzed against PBS buffer (10 mM in respect of phosphate, 140 mM in respect of sodium chloride, pH 7.4).

Dialysis and centrifugation gave 28 ml of a solution of modified SA containing 8.7 mg/ml, carrying an average of 16 monensins per mol of albumin.

EXAMPLE 7

Pharmacokinetics of the conjugate SA/monensin.

The pharmacokinetics were studied on male nude mice using the ionophoric conjugate described in Example 6.

The experimental protocol used is the same as that described in Example 5.

The results are given in FIG. 3, in which the time in hours has been plotted on the abscissa and the monensin concentration in μg/ml has been plotted on the ordinate. They show that:

1) as in the case of Example 5, the free monensin cannot be detected in the plasmas; and 2) the conjugate can be detected for at least 4 hours at a concentration of the order of 30 μg/ml. After 8 hours, the concentration found is now only of the order of 6 μg/ml. This concentration is nevertheless 400 times greater than that necessary for maximum activation under the conditions of the in vitro experiments.

EXAMPLE 8

Ionophoric conjugate obtained by reacting the fragment F(ab')₂ of the antibody anti-T65 substituted by an activated disulfide group with monensin into which a thiol has been introduced.

a) Fragment F(ab')₂ anti-T65

The fragment F(ab')₂ anti-T65 was obtained from the previously described antibody anti-T65 by enzymatic hydrolysis with the aid of pepsin. The antibody anti-T65 is dialyzed beforehand against 0.1M sodium formate buffer of pH 3.7 and 176 mg of antibody are then incubated in the presence of pepsin (0.05 mg of pepsin per mg of antibody) for 2 hours at 37° C. The enzyme reaction is then stopped with 2.05 ml of 2M tris buffer.

The solution is centrifuged and then purified by filtration on an ACA 44 column, the optical density of the effluent being measured at 280 nm. Concentration of the combined purified fractions gives 26 ml of a solution containing 3.3 mg/ml.

b) Activated fragment F(ab')$_2$ anti-T65

The product was obtained from the fragment F(ab')$_2$ described above by a technique analogous to that described for the antibodies in Example 1-b, giving 0.5 mg of F(ab')$_2$ anti-T65 possessing 34.3 activating groups per mol of antibody.

c) Activated Monensin

The monensin is activated by the method described in Example 1-c.

d) Preparation of the Ionophoric Conjugate 0.44 mg (i.e. 0.52 micromol) of monensin is dissolved in the minimum quantity of tert.-butanol and added to 1.02 ml of a solution of activated F(ab')$_2$ containing 0.33 mg/ml (i.e. 0.003 micromol) in 125 mM phosphate buffer of pH 7 in the presence of 54 µl of 1M hydroxylamine solution.

Incubation takes 1 hour at 25° C. and the reaction medium is then purified to remove excess reactants by dialysis against PBS buffer (10 mM in respect of phosphate, 140 mM in respect to sodium chloride, pH 7.4). Dialysis and centrifugation gave 1.1 ml of a solution of F(ab')$_2$ anti-T65 containing 0.33 mg/ml, carrying an average of 34 monensins per F(ab')$_2$.

EXAMPLE 9

Ionophoric conjugate obtained by reacting human serum albumin substituted by activated disulfide groups with, on the one hand, the antibody anti-DNP into which a thiol has been introduced, and, on the other hand, monensin into which a thiol has been introduced. The term anti-DNP antibodies denotes antibodies which are specifically directed against the 2,4-dinitrophenyl radical.

a) PREPARATION OF THE ANTIBODY ANTI-DNP

The anti-DNP antibodies used in this example are obtained according to the method disclosed in example 4 of FR patent 78/27838.

40 microliters of a solution of S-acetylmercaptosuccinic anhydride (SAMSA) containing 17 mg/ml in DMF are added to 30 mg of a solution of IgG anti-DNP containing 6.5 mg/ml, i.e. 0.2 micromol. The reaction medium is stirred for 2 hours and then purified to remove excess reactants by dialysis against 125 mM phosphate buffer of pH 7 for 24 hours at a rate of 400 ml/hour.

This gives 4.5 ml of a solution containing 6.4 mg/ml. By spectrophotometric analysis of the SH groups freed by reaction with hydroxylamine, it is found that the IgG obtained carries 4.4 SH groups per mol of antibody.

b) PREPARATION OF THE ACTIVATED SERUM ALBUMIN

The activated serum albumin was obtained from human serum albumin by a technique analogous to that described for the antibodies in the previous examples, giving 30 mg of serum albumin possessing 38 activating groups per mol of albumin.

c) ACTIVATED MONENSIN

The monensin is activated by the method described in Example 1-c.

d) PREPARATION OF THE IONOPHORIC CONJUGATE 3.5 ml of the solution of modified antibody anti-DNP (i.e. 0.149 micromol) are added to 4.1 ml of the solution of activated serum albumin obtained above (i.e. 0.450 micromol). 380 microliters of a 1N hydroxylamine solution are added and the mixture is then left to stand for 5 hours at 30° C. The reaction medium is purified by filtration on a column of SEPHADEX G200, the optical density being measured at 280 nm. The fractions containing both the antibody and the serum albumin are combined to give 16 ml of conjugate, which is purified to remove the excess free antibodies by passage through a column of DEAE tris-acryl (IBF). Elution is carried out in 0.02M tris buffer of pH 8.8 with the aid of an NaCl gradient from 0.035M to 0.1M, the optical density being measured at 280 nm.

The fractions containing both the antibody and the serum albumin (SAH) are combined, dialyzed against 125 mM phosphate buffer of pH 7 and then concentrated by ultrafiltration. This gives 12 ml of a solution of conjugate IgG/SAH. The average degree of coupling for this preparation, determined by electrophoretic densitometry, is 1.5 mol of serum albumin per mol of antibody.

4.86 mg of activated monensin (i.e. 5.76 micromol), dissolved in the minimum quantity of tert.-butanol, are added to this solution. 600 microliters of a 1N hydroxylamine solution are added, the mixture is left to stand for 1 hour at 25° C. and the reaction medium is then dialyzed against PBS buffer (10 mM in respect of phosphate +140 mM in respect of sodium chloride, pH 7.4).

Dialysis and centrifugation gave 13.5 ml of a solution of conjugate IgG/SAH containing 0.915 mg/ml, carrying an average of 26 monensins per IgG (i.e. 17.4 monensins per SAH).

EXAMPLE 10

Potentiation of the immunotoxin T65.

The conjugate according to the invention, obtained as indicated in Example 9, was studied for its capacity to potentiate the activity of the immunotoxin anti-T65 in the cell model described in Example 2.

In a first stage, the CEM cells may or may not be artificially labelled with TNP, i.e. the 2,4,6-trinitrophenyl group, which is the target molecule of the ionophoric conjugate.

In a second stage, these cells are incubated with the ionophoric conjugate and/or the immunotoxin anti-T65, after which the degree of inhibition of protein synthesis is measured by the method described in Example 2.

a) LABELLING OF THE CELLS WITH TNP

The labelling with TNP is carried out at +4° C. by the incubation of 2·10$^6$ CEM cells per ml of PBS buffer with an equal volume of a solution containing 10 mg/ml of sodium trinitrobenzenesulfonate. The reaction is stopped after 15 seconds by the addition of an excess of a 10$^{-3}$M solution of L-lysine; the cells are then washed.

b) MEASUREMENT OF THE DEGREE OF INHIBITION OF PROTEIN SYNTHESIS

The CEM cells which may or may not be labelled with TNP, at a concentration of $5 \cdot 10^5$ per ml, are preincubated for 1 hour at 4° C. with the ionophoric conjugate added at a concentration of $10^{-7}M$ in respect of antibodies. After washing at 4° C., the cells are resuspended in leucine-free RPMI-1640 medium containing 10% of thermally inactivated fetal calf serum and antibiotics, and the cells are then incubated for 20 hours at 37° C. in the presence of known concentrations of immunotoxin anti-T65. The cells are then subjected to the step for incorporation of the radioactive tracer.

c) ACTIVITY OF THE MONENSIN AFTER COUPLING (FIG. 4)

The unlabelled CEM cells are directly incubated with the immunotoxin at variable concentrations and with the coupled or uncoupled monensin introduced at a fixed concentration of $5 \cdot 10^{-8}M$. The potentiation of the cytotoxicity of the immunotoxin is identical in both cases, demonstrating that the coupling of the monensin does not affect its activating properties.

d) SPECIFICITY OF THE ACTIVATION OF THE IMMUNOTOXIN (IT) BY THE IONOPHORIC CONJUGATE (FIG. 5)

Curve 1 (control) shows that, after labelling of the cells with TNP, preincubation with the antibody anti-DNP at a concentration of $10^{-7}M$ and then incubation with the IT and the monensin at a concentration of $5 \cdot 10^{-8}M$, the potentiation of the IT by the ionophore is fully retained.

Curve 2 represents the cytotoxicity obtained by preincubation of the TNP-labelled cells with the ionophoric conjugate introduced at a concentration of $10^{-7}M$ in respect of antibodies, i.e. $2.6 \cdot 10^{-6}M$ in respect of monensin, followed by incubation with the immunotoxin. The $IC_{50}$ obtained is not notably different from the $IC_{50}$ obtained with the free monensin (curve 1).

Curve 3 represents the activity of the same ionophoric conjugate preincubated with the same cells except that they are not labelled with TNP.

A comparaison of curves 2 and 3 shows that the activation obtained with the ionophoric conjugate is very specific for the cells carrying the antigen (in this case the hapten TNP) corresponding to the antibody of the ionophoric conjugate. The specificity factor here is greater than 100.

Curve 4 shows the results obtained when the TNP-labelled cells are preincubated with the antibody anti-DNP and with the uncoupled monensin. The cytotoxicity of the immunotoxin is very low in this case and identical to that obtained under the same experimental conditions either on CEM cells not labelled with TNP (curve 5) or on TNP-labelled CEM cells preincubated with the antibody anti-DNP (curve 6). These control results confirm that it is indeed necessary for the monensin to be coupled with the antibody anti-DNP in order for selective activation to appear.

These results demonstrate the reality of a cytotoxic action, induced by double targeting towards the cells to be destroyed, with the aid of two different antibodies, on the one hand of the toxic constituent subunit of the immunotoxin and on the other hand of the activator used to increase the cytotoxic potential of the immunotoxin.

What is claimed is:

1. A conjugate comprising a monovalent carboxylic ionophore coupled by means of a covalent bond to a human protein, said conjugate functioning as an in vitro potentiator for immunotoxins.

2. A conjugate as claimed in claim 1 wherein the human protein is human serum albumin.

3. A conjugate as claimed in claim 1 wherein the covalent bond coupling the carboxylic ionophore and the human protein is a disulfide or thioether bond.

4. A conjugate as claimed in claim 1 wherein the ionophore contains a primary hydroxyl group.

5. A conjugate comprising a monovalent carboxylic ionophore coupled by means of a covalent bond to a monoclonal antibody or a fragment thereof, wherein the antibody fragment is Fab, Fab' or F(ab')$_2$ fragment of an immunoglobulin, said conjugate functioning as an in vitro potentiator for immunotoxins.

6. A conjugate comprising a monovalent carboxylic ionophore coupled by means of a covalent bond to a mixed macromolecule, which is obtained by a covalent coupling between an antibody or a fragment thereof and a protein, said conjugate functioning as an in vitro potentiator for immunotoxins.

7. A conjugate as claimed in claim 6 wherein the protein is human serum albumin.

8. A conjugate as claimed in claim 6 wherein the covalent bond coupling the carboxylic ionophore and the macromolecule is a disulfide or a thioether bond.

9. A conjugate as claimed in claim 6 wherein the ionophore contains a primary hydroxyl group.

10. A conjugate as claimed in claim 1 wherein the ionophore is monensin or nigericin.

11. A conjugate comprising a monovalent carboxylic ionophore coupled by means of a covalent bond to a macromolecule, said conjugate functioning to potentiate immunotoxins in in vitro conditions.

12. A conjugate as claimed in claim 11 wherein the macromolecule is an antibody, a peptide hormone, a human protein, a peptide ligand or a mixed macromolecule.

13. A conjugate as claimed in claim 11 wherein the monovalent carboxylic ionophore is from monensin or nigericin.

14. A conjugate as claimed in claim 11 wherein the covalent bond coupling the carboxylic ionophore and the macromolecule is a disulfide bond or a thioether.

15. A conjugate as claimed in claim 11 wherein said in vitro conditions apply to human bone marrow treatment in view of subsequent bone marrow autologous or allogeneic bone marrow transplantation.

16. A process for the preparation of a conjugate which potentiates immunotoxins in in vitro conditions which comprises a monovalent carboxylic ionophore coupled by means of a covalent bond to a macromolecule which comprises:
   1) introducing a thiol group into one of the compounds to be coupled;
   2) introducing into the other compound one or more groups capable of reaction with the said thiol group; and
   3) reacting the two resulting compounds in an aqueous medium, at a pH between 5 and 9, at a temperature below 30° C.

17. A conjugate comprising a monovalent carboxylic ionophore which is monensin or nigericin coupled by means of a covalent bond to a macromolecule, said conjugate functioning to potentiate immunotoxins in in vitro conditions.

* * * * *